United States Patent [19]

Wray

[11] Patent Number: 5,215,092
[45] Date of Patent: Jun. 1, 1993

[54] ULTRASONIC PROBE ASSEMBLY
[75] Inventor: Terry A. Wray, McClure, Pa.
[73] Assignee: Interspec, Inc., Ambler, Pa.
[21] Appl. No.: 840,835
[22] Filed: Feb. 25, 1992
[51] Int. Cl.⁵ ................................................. A61B 8/12
[52] U.S. Cl. ........................... 128/660.09; 128/662.03; 128/662.06; 128/661.01; 128/4
[58] Field of Search ...................... 128/662.03, 662.06, 128/660.09, 660.10, 661.01, 4

[56]  References Cited
U.S. PATENT DOCUMENTS

| | | | |
|---|---|---|---|
| 4,272,991 | 6/1981 | Cribbs | 128/660.09 |
| 4,374,525 | 2/1983 | Baba | 128/662.06 |
| 4,375,818 | 3/1983 | Suwaki et al. | 128/662.06 |
| 4,401,123 | 8/1983 | Baba | 128/662.06 |
| 4,483,326 | 11/1984 | Yarnaka et al. | 128/4 |
| 4,535,781 | 8/1985 | Metz | 128/662.03 |
| 4,543,960 | 10/1985 | Harvi et al. | 128/662.06 |
| 4,756,313 | 7/1988 | Terwilliger | 128/660.11 |
| 4,834,102 | 5/1959 | Schwarzchild et al. | 128/662.06 |
| 4,930,515 | 6/1990 | Terwilliger | 128/662.06 |
| 5,050,610 | 9/1991 | Oaks et al. | 128/660.06 |
| 5,085,221 | 2/1992 | Ingebrigtsen et al. | 128/662.06 |

FOREIGN PATENT DOCUMENTS 38296039 9/1988 Fed. Rep. of Germany ......................... 128/660.01

OTHER PUBLICATIONS

"Esophagel Echocardiography" by L. Frazin et al., Circulation, vol. 54, No. 1, pp. 102-108 (Jul. 1976).
"Transoesophageal Cross-sectional Echocardiography ... System", by M. Schluter et al, Transoesophageal 2D echo, 48:67-72 (Jul., 1982).
"Cardiovascular Radiology: New Equipment ... Afternoon", by William J. Casarella et al, Abstract at the 52nd Scient. Sessions, II-45 (Oct. 1979).
"An Endoscopic Micromanipulator for Multiplanar Tronsesophageal Imaging" by Roy W. Martin et al., Ultrasound in Medicine and Biology, vol. 12, No. 12, pp. 965-975, Dec. 1986.

Primary Examiner—Kyle L. Howell
Assistant Examiner—George Manuel
Attorney, Agent, or Firm—Ratner and Prestia

[57]  ABSTRACT

An ultrasonic probe assembly in which the disposition of the scan plane of an ultrasonic transducer unit, introduced into a human body, can be selected to image a body part in different ways. The scan plane is selected by operation of a remote control unit by which the ultrasonic array is moved. The ultrasonic array is mounted to a base unit for pivotal movement relative to the base unit and is steered by the action of a cable which is controlled by the remote control unit.

23 Claims, 2 Drawing Sheets

ULTRASONIC PROBE ASSEMBLY

TECHNICAL FIELD

The present invention relates, in general, to ultrasonic imaging and, in particular, to a probe in which the scan plane of an ultrasonic transducer unit, positioned within a body cavity, can be changed by controls outside the body, so that a body organ, such as the heart, which is being imaged can be viewed in different ways (i.e. in longitudinal and transverse sections or any section in between). Such a probe often is referred to as a "multiplane" probe by those skilled in the art.

BACKGROUND OF THE INVENTION

Many different ultrasonic multi-plane probes, arranged for positioning within the body, have been suggested or put into actual use in the past. Depending upon the design, there are a number of shortcomings with this general class of prior art ultrasonic multi-plane probes.

Certain of these prior art ultrasonic multi-plane probes are arranged with the ultrasonic transducer array located within a cylindrical housing. Generally, these probes are larger than desired and cleaning is a problem. Although these probes are small to begin with, even smaller probes are desirable. Those engaged in the design and development of ultrasonic multi-plane probes are faced with the apparent conflicting requirements of providing as large an ultrasonic array as possible to increase resolution of the imaging and as small a housing for the ultrasonic array and other components as possible to facilitate passage of the unit through the body of a patient to the body cavity where the imaging is to be done. By containing the ultrasonic transducer array within a housing, the length and width dimensions of the housing are dependent upon the size of the ultrasonic transducer array. Also, by containing the ultrasonic transducer array within a housing, cleaning this component can be more difficult than desired.

Another problem with most of the prior art ultrasonic multi-plane probes which are arranged for positioning within the body and of which applicant is aware is the difficulty in positioning the probes in the body cavity to develop the desired high-quality images of the body organs being imaged. This problem also is due to the size of the probe. For example, in transesophageal imaging of the heart, the probe should be positioned as close as possible to and preferably in contact with the wall of the esophagus. The larger the probe, the more difficult to maneuver the probe into the desired position.

It is common practice, in the design of these probes, to fill the cavity in which the ultrasonic transducer array unit is located with a fluid and to cover the cavity with a membrane. The fluid is provided in such probes to establish the proper acoustic coupling from the array into the membrane. The very presence of the fluid in the cavity in the probe housing is the source of potential damage to the ultrasonic transducer array caused by swelling or corrosion due to the presence of the fluid in the cavity.

Yet another problem with most of the prior art ultrasonic multi-plane probes which are arranged for positioning within the body and of which applicant is aware is that the membrane cover, which is an added component in the acoustic path, can attenuate and distort sound waves in a manner which reduces ultrasound system resolution.

In addition to the foregoing, another problem with most of these prior art multi-plane probes known to applicant is that the positioning mechanism passes through seals which are susceptible to leakage of body fluids into the probe cavity to contaminate the fluid in the probe cavity possibly leading to corrosion and acoustic problems. Leakage of the probe cavity fluid into the patient also can occur, but this problem is overcome by using biocompatible fluid in the probe cavity.

SUMMARY OF THE INVENTION

An ultrasonic probe assembly, constructed in accordance with the present invention, includes a base unit and ultrasonic transducer means for scanning in a scan plane. The ultrasonic transducer means are mounted to the base unit so that the emitting surface of the ultrasonic transducer means at which an ultrasound beam is formed is external to the base unit and the ultrasonic transducer means are pivotally movable relative to the base unit through a positioning angle which extends in a plane perpendicular to the scan plane, thereby changing the disposition of the scan plane. An ultrasonic probe assembly, constructed in accordance with the present invention, also includes a means for selecting an angular position of the ultrasonic transducer means corresponding to a selected disposition of the scan plane of the ultrasonic transducer means and means extending from the angular position selecting means through the base unit to the ultrasonic transducer means and responsive to the angular position selecting means for moving the ultrasonic transducer means to the selected angular position.

DETAILED DESCRIPTION OF THE INVENTION

Figure 1:
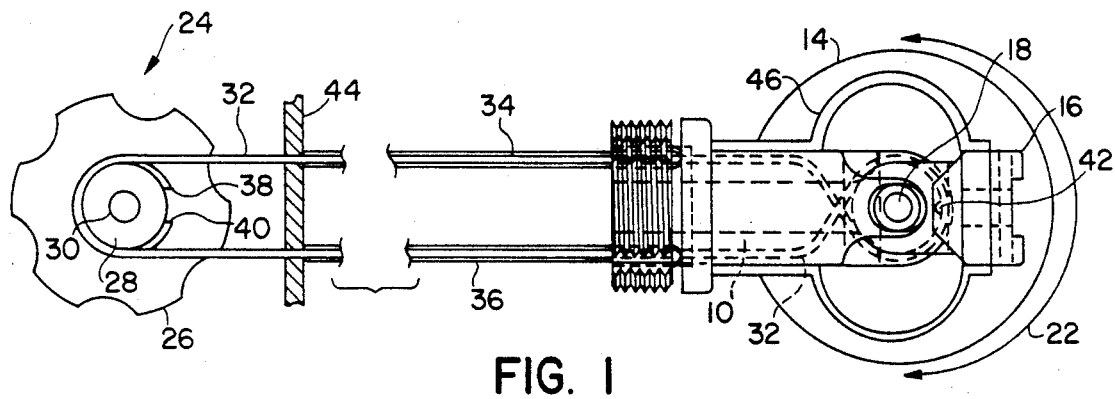
FIG. 1 is a horizontal sectional view of the probe portion and a plan view of the remote control portion of one preferred embodiment of an ultrasonic probe assembly constructed in accordance with the present invention.
Figure 2:
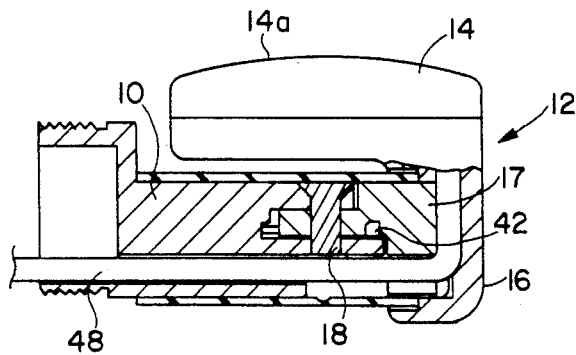
FIG. 2 is a vertical sectional view of the probe portion of FIG. 1.
Figure 3:
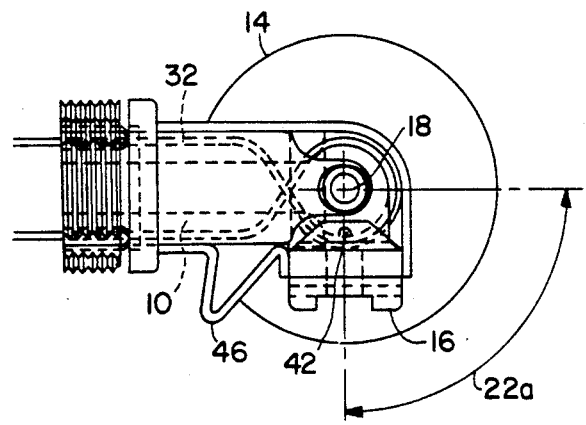
FIG. 3 is a horizontal sectional view, generally similar to FIG. 1, of the probe portion of FIG. 1 with the angular position of the ultrasonic array of the ultrasonic probe assembly rotated ninety degrees from its position illustrated in FIG. 1.

Referring to FIGS. 1 through 3, one preferred embodiment of an ultrasonic probe assembly, constructed in accordance with the present invention, includes a base unit 10 and an ultrasonic array unit 12 which, in turn, includes an ultrasonic array 14, an array mount 16 upon which the ultrasonic array is mounted and a pivot arm 17 to which the array mount is fixed. Ultrasonic array 14 can be of conventional construction and operation, preferably a multi-element phased array ultrasonic transducer, which forms an ultrasonic beam which is emitted from surface 14a of the ultrasonic array and is scanned in a plane projecting out of the paper for FIGS. 1 and 3. As shown in FIG. 2, array mount 16 is, for the embodiment of the invention being described, in the form of a right-angle elbow.

Ultrasonic array unit 12 is mounted to base unit 10 by means of a pivot pin 18 which extends through pivot arm 17 into base unit 10 to either side of the pivot arm. As shown most clearly in FIG. 2, emitting surface 14a of the ultrasonic transducer means, at which the ultrasound beam is formed, is external to base unit 10. Ultrasonic array unit 12, including ultrasonic array 14, is pivotally movable relative to the base unit through a positioning angle which extends in a plane perpendicular to the scan plane of the ultrasonic array, namely in the plane of the paper for FIGS. 1 and 3, to change the disposition of the scan plane. The plane of the positioning angle of ultrasonic array unit 12 is perpendicular to the pivot axis of pivot pin 18. Pivotal movement of ultrasonic array unit 12 is represented by an arrow 22 in FIG. 1. For the embodiment of the invention being described, the range of scan plane variation is one-hundred and eighty degrees. Ultrasonic array 14 can be moved ninety degrees clockwise, as shown in FIG. 3, from its center position, as shown in FIG. 1, and ninety degrees counterclockwise from its center position. An arrow 22a in FIG. 3 represents the ninety degrees clockwise movement of ultrasonic array 14 from its center position.

An ultrasonic probe assembly, constructed in accordance with the present invention, further includes a remote control unit 24 for selecting an angular position of ultrasonic array unit 12 corresponding to a selected disposition of the scan plane of ultrasonic array 14. For the embodiment of the invention being described, remote control unit 24 includes a knob 26, a pulley 28 and a shaft 30 on which the knob and the pulley are rotatably mounted, so that upon turning the knob to a selected position, the position of the pulley is controlled and the pulley will be turned a corresponding amount.

An ultrasonic probe assembly, constructed in accordance with the present invention, further includes position control means which extend from remote control unit 24 through base unit 10 to ultrasonic array unit 12 and are responsive to the remote control unit for moving the ultrasonic array unit to a selected angular position. For the embodiment of the invention being described, the position control means include a cable 32 having a first length slidable within a jacket 34 and a second length slidable within a jacket 36. The ends 38 and 40 of cable 32 are attached to pulley 28 of remote control unit 24 and the midpoint 42 of cable 32 is attached to pivot arm 17 of ultrasonic array unit 12. Jackets 34 and 36 of cable 32 are attached to base unit 10 and a wall 44 of remote control unit 24. As seen most clearly from FIGS. 1 and 3, the lengths of cable 32 are arranged so that they cross over one another before making contact with pivot arm 17. This arrangement results in less strain on the cable and less slack in the cable.

As knob 26 is turned in a first direction (i.e. clockwise), cable 32, attached to pivot arm 17, steers ultrasonic array unit 12 to turn about pivot pin 18 in a pivotal first direction (i.e. counterclockwise) and as knob 26 is turned in a second and opposite direction (i.e. counterclockwise), cable 32 steers ultrasonic array unit 12 to turn about pivot pin 18 in a pivotal second and opposite direction (i.e. clockwise). In this way, ultrasonic array 14 can be moved to any position between the ends of arrow 22 in FIG. 1 to image a selected body part at a selected scan plane.

A flexible protective sleeve 46 preferably is included in the embodiment of the invention being described. Sleeve 46 is attached at one of its ends to base unit 10 and at its other end to array mount 16 of ultrasonic array unit 12. Sleeve 46 is shaped with oppositely disposed semi-circular sections, so that as ultrasonic array unit 12 pivots from its center position, one semi-circular section moves to fit snugly around array mount 16, while the other section folds over itself. This is seen most clearly by comparing the shape of sleeve 46 in FIG. 1 with the shape of the sleeve in FIG. 3.

Electrical signals are conducted to and from ultrasonic array 14 by means of a bundle of wires 48 which extend through base unit 10 and array mount 14 of ultrasonic array unit 12 and are connected to the ultrasonic array. In particular, wires 48 extend through a passage beneath pivot pin 18 and parallel to the axis of the pivot pin through a passage in right-angle elbow 14 to the ultrasonic array. With this arrangement of wire bundle 48 passing beneath pivot pin 18 and up through array mount 14, the individual wires are subjected to minimal bending stresses as the scan plane disposition of the ultrasonic array is being changed.

Figure 4:
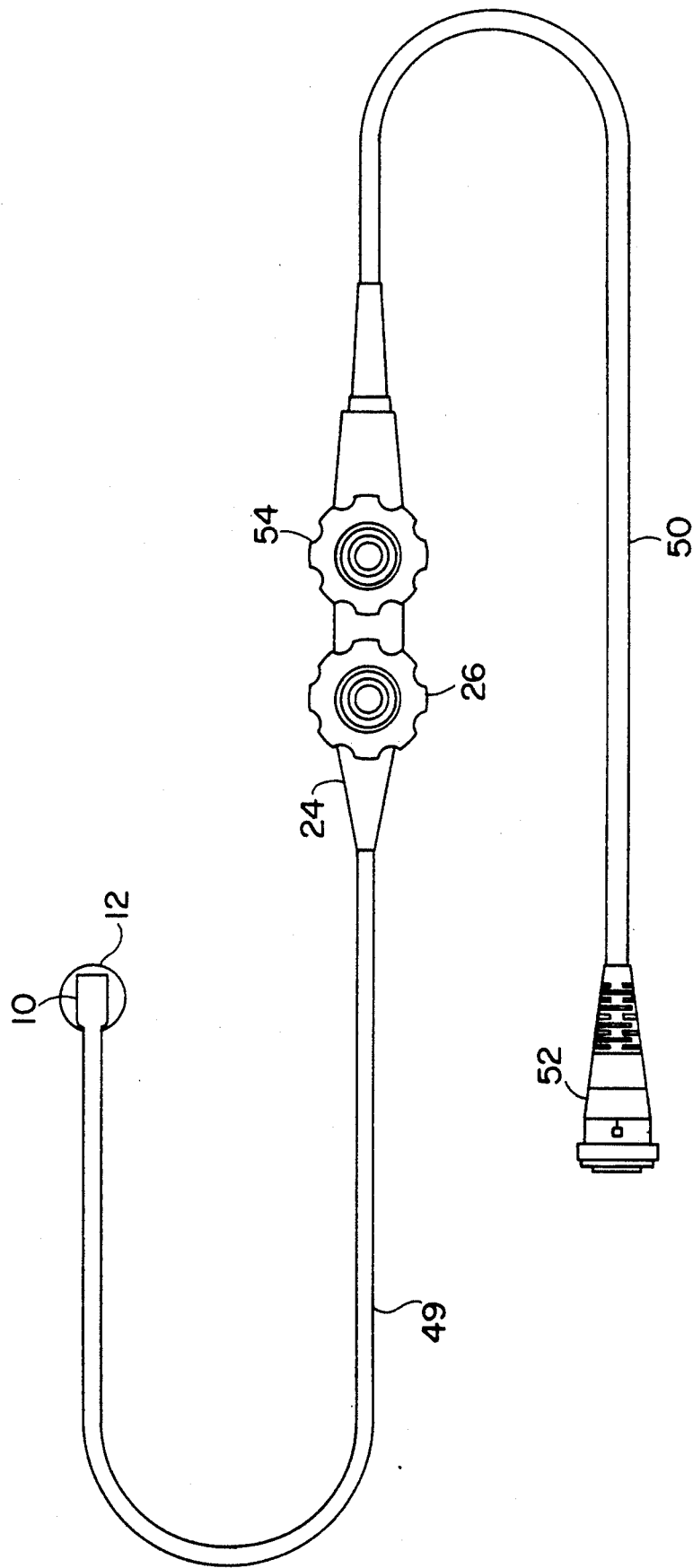
FIG. 4 is a plan view of an endoscope in which the ultrasonic probe assembly of FIGS. 1 through 3 can be incorporated.

FIG. 4 illustrates the ultrasonic probe assembly of FIGS. 1 through 3 incorporated in an endoscope. Base unit 10 and ultrasonic array unit 12 are connected mechanically to remote control unit 24 by cable 32 (not shown in FIG. 4) and jackets 34 and 36 (not shown in FIG. 4) which extend within a flexible endoscope shaft 49, one end of which is threadedly attached to base unit 10. Electrical signals are conducted to and from ultrasonic array unit 12 by wires (also not shown in FIG. 4) which also extend within flexible endoscope shaft 49 and a cable 50 having a connector 52 at one end which is adapted for connection into suitable signal processing and imaging equipment. A second knob 54 on remote control unit 24 controls bending of the end of the endoscope shaft 49 upward, downward and sideways to permit the end of the endoscope to make turns as it is passed through the throat, for example, to enter the esophagus to image the heart.

The location of ultrasonic array 14 external to base unit 10, with the ultrasonic array pivotally movable relative to the base unit, allows for improved positioning of the probe portion of the probe assembly and the use of larger ultrasonic arrays, both of which contribute to improved imaging. The external ultrasonic array permits the operator of the probe assembly to position the probe portion, including the ultrasonic array, with more of the scanning surface of the ultrasonic array in contact with or proximity to the body part being imaged, as compared to comparable prior art imaging probes. Generally, in such prior art probes, in which the pivotally mounted ultrasonic array is located within the probe housing, the physical arrangement of the probe (i.e. shape and dimensions) often results in excessive spacing between the ultrasonic array and the body part being imaged. This affects the quality of the image of the body part. By locating the ultrasonic array outside the probe housing, maneuverability of the ultrasonic array into proximity with the body part being imaged is easier because the probe housing can be spaced from the body part being imaged and only the proximity of the ultrasonic array to the body part is of concern.

The external, pivotally mounted ultrasonic array of the present invention also allows a larger array to be used. Probe designs having a pivotally mounted ultrasonic array within the probe housing require that the probe housing have a diameter which is equal to at least the length of the array. This limits the length of the ultrasonic array to the maximum cross-section of a probe which can be inserted into and removed from a patient. With the present invention, the ultrasonic array can be oriented longitudinally for insertion and removal and, while in the body of the patient, can be pivoted to image the desired section of the body part, thereby allowing a larger ultrasonic array for improved imaging.

The foregoing has set forth an exemplary and preferred embodiment of the present invention. It will be understood, however, that various other alternative embodiments will occur to those of ordinary skill in the art without departure from the spirit and scope of the present invention.

What is claimed:

1. An ultrasonic probe assembly comprising:
   a base unit;
   an ultrasonic array unit including:
   (a) an ultrasonic array for scanning in a scan plane, and
   (b) an array mount upon which said ultrasonic array is mounted,
   means for mounting said ultrasonic array unit to said base unit with said ultrasonic array external to said base unit for pivotal movement of said ultrasonic array unit about a single point fixed relative to said base unit and through a positioning angle extending in a plane perpendicular to said scan plane to change the disposition of said scan plane;
   a remote control unit for selecting an angular position of said ultrasonic array unit corresponding to a selected disposition of said scan plane of said ultrasonic array;
   and position control means extending from said remote control unit through said base unit to said ultrasonic array unit and responsive to said remote control unit for moving said ultrasonic array unit to said selected angular position.

2. An ultrasonic probe assembly according to claim 1 wherein said ultrasonic array unit further includes a pivot arm to which said array mount is fixed and said mounting means include a pivot pin extending through said pivot arm into said base unit to either side of said pivot arm.

3. An ultrasonic probe assembly according to claim 2 further including means extending through said base unit to said ultrasonic array for conducting electrical signals to and from said ultrasonic array.

4. An ultrasonic probe assembly according to claim 3 wherein said array mount is a right-angle elbow.

5. An ultrasonic probe assembly according to claim 4 wherein said electrical signal conducting means include a bundle of wires extending through said base unit and said right-angle elbow to said ultrasonic array.

6. An ultrasonic probe assembly according to claim 5 wherein said bundle of wires extend beneath said pivot pin and through said right-angle elbow parallel to the axis of said pivot pin.

7. An ultrasonic probe assembly according to claim 6 wherein said ultrasonic array unit is mounted for pivotal movement over an angle of one-hundred and eighty degrees.

8. An ultrasonic probe assembly according to claim 7 further including a flexible sleeve extending between said base unit and said right-angle elbow.

9. An ultrasonic probe assembly comprising:
   a base unit;
   an ultrasonic array;
   mounting means for mounting said ultrasonic array to said base unit with said ultrasonic array external to said base unit for pivotal movement of said ultrasonic array about a single point fixed relative to said base unit;
   selection means extending through said base unit and connected to said mounting means for setting a selected pivotal position of said ultrasonic array;
   and means extending through said base unit to said ultrasonic array for conducting electrical signals to and from said ultrasonic array.

10. An ultrasonic probe assembly according to claim 9 wherein said selection means include:
    (a) a remote control unit for selecting an angular position of said ultrasonic array corresponding to a selected disposition of said scan plane of said ultrasonic array, and
    (b) a cable extending between said remote control unit and said mounting means.

11. An ultrasonic probe assembly comprising:
    a base unit;
    ultrasonic transducer means for forming an ultrasound beam at an emitting surface and for scanning said ultrasound beam in a scan plane;
    mounting means for mounting said ultrasonic transducer means to said base unit with said emitting surface of said ultrasonic transducer means external to said base unit for pivotal movement of said ultrasonic transducer means unit about a single point fixed relative to said base unit and through a positioning angle extending in a plane perpendicular to said scan plane to change the disposition of said scan plane;
    a remote control unit for selecting an angular position of said ultrasonic transducer means corresponding to a selected disposition of said scan plane of said ultrasonic transducer means;
    and position control means extending from said remote control unit through said base unit to said ultrasonic transducer means and responsive to said remote control unit for moving said ultrasonic transducer means to said selected angular position.

12. An ultrasonic probe assembly comprising:
    a base unit;
    ultrasonic transducer means for scanning in a scan plane;
    mounting means for mounting said ultrasonic transducer means to said base unit with said ultrasonic transducer means external to said base unit for pivotal movement of said ultrasonic transducer means unit about a single point fixed relative to said base unit and through a positioning angle extending in a plane perpendicular to said scan plane to change the disposition of said scan plane;
    a remote control unit for selecting an angular position of said ultrasonic transducer means corresponding to a selected disposition of said scan plane of said ultrasonic transducer means;
    and position control means extending from said remote control unit through said base unit to said ultrasonic transducer means and responsive to said remote control unit for moving said ultrasonic transducer means to said selected angular position.

13. An endoscope comprising:
    an ultrasonic array unit including:

(a) an ultrasonic array for scanning in a scan plane, and (b) an array mount upon which said ultrasonic array is mounted, means for mounting said ultrasonic array unit to said base unit with said ultrasonic array external to said base unit for pivotal movement of said ultrasonic array unit about a single point fixed relative to said base unit and through a positioning angle extending in a plane perpendicular to said scan plane to change the disposition of said scan plane;

a remote control unit for selecting an angular position of said ultrasonic array unit corresponding to a selected disposition of said scan plane of said ultrasonic array;

position control means extending from said remote control unit through said base unit to said ultrasonic array unit and responsive to said remote control unit for moving said ultrasonic array unit to said selected angular position;

and means for connecting said remote control unit to signal processing and imaging equipment.

14. An endoscope according to claim 13 wherein said ultrasonic array unit further includes a pivot arm to which said array mount is fixed and said mounting means include a pivot pin extending through said pivot arm into said base unit to either side of said pivot arm.

15. An endoscope according to claim 14 further including means extending through said base unit to said ultrasonic array for conducting electrical signals to and from said ultrasonic array.

16. A endoscope according to claim 15 wherein said array mount is a right-angle elbow.

17. An endoscope according to claim 16 wherein said electrical signal conducting means include a bundle of wires extending through said base unit and said right angle elbow to said ultrasonic array.

18. An endoscope according to claim 17 wherein said bundle of wires extend beneath said pivot pin and through said right-angle elbow parallel to the axis of said pivot pin.

19. An endoscope according to claim 18 wherein said ultrasonic array unit is mounted for pivotal movement over an angle of one-hundred and eighty degrees.

20. An endoscope according to claim 19 further including a flexible sleeve extending between said base unit and said right-angle elbow.

21. An ultrasonic probe assembly comprising:

a base unit;

an ultrasonic array;

mounting means for pivotally mounting said ultrasonic array to said base unit with said ultrasonic array external to said base unit;

selection means extending through said base unit and connected to said mounting means for setting a selected pivotal position of said ultrasonic array, including:

(a) a remote control unit for selecting an angular position of said ultrasonic array corresponding to a selected disposition of said scan plane of said ultrasonic array, and (b) a cable extending between said remote control unit and said mounting means, said cable having two ends both of which are attached to said remote control unit and having a midpoint attached to said mounting means; and means extending through said base unit to said ultrasonic array for conducting electrical signals to and from said ultrasonic array.

22. An ultrasonic probe assembly according to claim 21 that length of said cable between one of said ends and said midpoint crosses over that length of said cable between said other end and said midpoint.

23. An ultrasonic probe assembly according to claim 22 wherein said remote control unit includes rotatable knob for selecting the scan plane of said ultrasonic array and to which said ends of said cable are coupled.

* * * * *